US008062490B2

(12) United States Patent
Bell et al.

(10) Patent No.: US 8,062,490 B2
(45) Date of Patent: *Nov. 22, 2011

(54) REAGENT COMPOSITIONS FOR USE IN ELECTROCHEMICAL DETECTION

(75) Inventors: Douglas E. Bell, Coral Springs, FL (US); Michele Albino, North Lauderdale, FL (US)

(73) Assignee: Nipro Diagnostics, Inc., Ft. Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/724,280

(22) Filed: Mar. 15, 2010

(65) Prior Publication Data

US 2010/0227355 A1    Sep. 9, 2010

Related U.S. Application Data

(63) Continuation of application No. 12/017,496, filed on Jan. 22, 2008, now Pat. No. 7,678,250.

(51) Int. Cl.
*G01N 27/327* (2006.01)
*G01N 21/00* (2006.01)
(52) U.S. Cl. .............. 204/403.04; 204/403.11; 422/420
(58) Field of Classification Search .............. 204/403.01–403.15; 205/777.5, 205/778, 792; 422/420, 425
See application file for complete search history.

(56) References Cited

U.S. PATENT DOCUMENTS

| 5,036,000 A | 7/1991 | Palmer et al. |
| 5,264,092 A | 11/1993 | Skotheim et al. |
| 7,678,250 B2 * | 3/2010 | Bell et al. ................. 204/403.04 |
| 2007/0080073 A1 | 4/2007 | Wu et al. |

FOREIGN PATENT DOCUMENTS

| WO | WO 02/14535 A2 | 2/2002 |
| WO | WO 2005/040407 A1 | 5/2005 |

OTHER PUBLICATIONS

CAPLUS abstract of BR 2002004378 A, patent published Jun. 1, 2004.
CAPLUS abstract of BR 2002005463 A, patent published Jul. 27, 2004.
Sciencelab.com entry for Meldola's Blue downloaded on Aug. 14, 2009.
International Search Report and Written Opinion, PCT/US2009/031190, mailed Jul. 17, 2009.
Office Action/Restriction Requirement in parent U.S. Appl. No. 12/017,496, mailed Apr. 17, 2009.
Office Action in parent U.S. Appl. No. 12/017,496, mailed Aug. 19, 2009.
Notice of Allowance in parent U.S. Appl. No. 12/017,496, mailed Nov. 6, 2009.

* cited by examiner

*Primary Examiner* — Alex Noguerola
(74) *Attorney, Agent, or Firm* — Finnegan, Henderson, Farabow, Garrett & Dunner, L.L.P.

(57) ABSTRACT

Biological reagent compositions with improved sensitivity to the concentration of blood glucose in patient samples for use in measuring systems and methods. The reagent compositions comprise a glucose oxidoreductase enzyme, a flavin nucleoside coenzyme and a mediator formulation. The mediator formulation comprises at least one electroactive organic molecule and at least one coordination complex.

22 Claims, 1 Drawing Sheet

REAGENT COMPOSITIONS FOR USE IN ELECTROCHEMICAL DETECTION

CROSS-REFERENCE TO RELATED APPLICATION

This application is a continuation of U.S. patent application Ser. No. 12/017,496, filed Jan. 22, 2008, which is now U.S. Pat. No. 7,678,250, both of which are incorporated herein by reference in their entireties for all purposes.

FIELD OF THE INVENTION

The present invention relates to electrochemical sensors and, more particularly, to systems and methods for electrochemically sensing blood glucose levels.

BACKGROUND OF THE INVENTION

Many industries have a commercial need to monitor the concentration of particular constituents in a fluid. The oil refining industry, wineries, and the dairy industry are examples of industries where fluid testing is routine. In the health care field, there are numerous examples of the need to monitor a particular constituent within bodily fluids. A number of systems are available that allow testing of body fluid, such as, blood, urine, or saliva, to conveniently monitor the level of a particular fluid constituent, such as, for example, cholesterol, proteins, and glucose. Patients suffering from diabetes, a disorder of the pancreas where insufficient insulin production prevents the proper digestion of sugar, must carefully monitor their blood glucose levels on a daily basis. A number of systems that allow people to conveniently monitor their blood glucose levels are available. Such systems typically include a test strip where the user applies a blood sample and a meter that "reads" the test strip to determine the glucose level in the blood.

Among the various technologies available for measuring blood glucose levels, electrochemical technologies are particularly desirable because only a very small blood sample may be needed to carry out the measurement. In electrochemical-based systems, the test strip typically includes a sample chamber that contains reagents, such as glucose oxidase and a mediator, and electrodes. When the user applies a blood sample to the sample chamber, the reagents react with the glucose, and the meter applies a voltage to the electrodes to cause a redox reaction. The meter measures the resulting current and calculates the glucose level based on the current.

In a typical electrochemical sensor, regardless of the size of the system, the oxidation or reduction half-cell reaction involving glucose either produces or consumes electrons. This electron flow can be measured, provided the electrons can interact with a working electrode that is in contact with the sample to be analyzed. The electrical circuit is completed through a counter electrode that is also in contact with the sample. A chemical reaction occurs at the counter electrode, and this reaction (oxidation or reduction) is the opposite of the reaction at the working electrode. See, for example, *Fundamentals Of Analytical Chemistry*, 4$^{th}$ Edition, D. A. Skoog and D. M. West; Philadelphia: Saunders College Publishing (1982), pp 304-341.

Another feature of some conventional miniaturized electrochemical test strips is the presence of a single layer of biological reagents over both the working and counter electrodes. The components of this reagent layer include the enzyme that facilitates the oxidation-reduction reaction of glucose, a coenzyme, and any mediators or other substances that help to transfer electrons between the oxidation-reduction reaction and the working electrode. The use of a single reagent layer can provide for simple manufacturing of the strips, since only one deposition step is needed to coat the material onto the electrodes. However, due to the biological nature of the reagent layer, it is difficult to reproducibly manufacture each strip with the exact same sensitivity. In addition, most reagent compositions exhibit vastly different electrochemical properties. The best reagent compositions are those that exhibit increased sensitivity by facilitating the free flow of electrons between the sample being analyzed and the electrode and its connected circuitry.

Accurate measurement of blood glucose levels may be critical to the long-term health of many users. As a result, meters and test strips used to measure blood glucose levels should be highly reliable. However, as sample sizes become smaller, the dimensions of the sample chamber and electrodes in the test strip also become smaller. This, in turn, may make test strips more susceptible to smaller manufacturing defects and to damage from subsequent handling.

Accordingly, the present invention provides improved biological reagent compositions with improved sensitivity to the concentration of blood glucose in patient samples for use in measuring systems and methods, whereby a relatively constant linear relationship exists between the measured current and the glucose concentration for the time scale of the analysis.

SUMMARY OF THE INVENTION

In a first principal aspect, the present invention provides a reagent layer for a test strip for testing a blood sample. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a phenoxazine or a phenoxazinium salt, and at least one coordination complex.

In a second principal aspect, the present invention provides a reagent layer for a test strip for testing a blood sample. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a benzophenoxazine or a benzophenoxazinium salt and at least one coordination complex independently selected from iron, osmium or ruthenium complexes.

In a third principal aspect, the present invention provides a reagent layer for a test strip for testing a blood sample. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a benzophenoxazine or a benzophenoxazinium salt and at least one ruthenium coordination complex.

In a fourth principal aspect, the present invention provides a reagent layer for a test strip for testing a blood sample. The reagent layer comprises a glucose oxidoreductase, a flavin nucleoside coenzyme and/or a nicotinamide nucleotide coenzyme, and a mediator formulation. The mediator formulation comprises at least one electroactive organic molecule and at least one coordination complex. The at least one electroactive organic molecule is independently selected from 9-(dimethylamino)benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine. The at least one coordination complex is ruthenium hexamine.

In a fifth principal aspect, the present invention provides a reagent layer for a test strip for testing a blood sample. The reagent layer comprises glucose dehydrogenase, flavin adenine dinucleotide and/or a nicotinamide nucleotide coenzyme, and a mediator formulation. The mediator formulation comprises at least one electroactive organic molecule independently selected from a benzophenoxazine or a benzophenoxazinium salt and at least one ruthenium coordination complex.

In a sixth principal aspect, the present invention provides a test strip for testing a blood sample. The test strip comprises a base, a sample chamber for the blood sample, at least one working electrode, at least one counter electrode, and a reagent layer. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a phenoxazine or a phenoxazinium salt, and at least one coordination complex.

In a seventh principal aspect, the present invention provides a test strip for testing a blood sample. The test strip comprises a base, a sample chamber for the blood sample, at least one working electrode, at least one counter electrode, and a reagent layer. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a benzophenoxazine or a benzophenoxazinium salt, and at least one coordination complex independently selected from iron, osmium or ruthenium complexes.

In a eighth principal aspect, the present invention provides a test strip for testing a blood sample. The test strip comprises a base, a sample chamber for the blood sample, at least one working electrode, at least one counter electrode, and a reagent layer. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a benzophenoxazine or a benzophenoxazinium salt and at least one ruthenium coordination complex.

In a ninth principal aspect, the present invention provides a test strip for testing a blood sample. The test strip comprises a base, a sample chamber for the blood sample, at least one working electrode, at least one counter electrode, and a reagent layer. The reagent layer comprises a glucose oxidoreductase, a flavin nucleoside coenzyme and/or a nicotinamide nucleotide coenzyme, and a mediator formulation. The mediator formulation comprises at least one electroactive organic molecule and at least one coordination complex. The at least one electroactive organic molecule is independently selected from 9-(dimethylamino)benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine. The at least one coordination complex is ruthenium hexamine.

In a tenth principal aspect, the present invention provides a test strip for testing a blood sample. The test strip comprises a base, a sample chamber for the blood sample, at least one working electrode, at least one counter electrode, and a reagent layer. The reagent layer comprises glucose dehydrogenase, flavin adenine dinucleotide and/or a nicotinamide nucleotide coenzyme, and a mediator formulation. The mediator formulation comprises at least one electroactive organic molecule independently selected from a benzophenoxazine or a benzophenoxazinium salt and at least one ruthenium coordination complex.

In a eleventh principal aspect, the present invention provides a method of making a test strip for testing a blood sample. The method comprises depositing a first electrode on a base; depositing a second electrode on the base; and applying a reagent layer on the base covering at least a portion of at least first or second electrode. The reagent layer comprises a glucose oxidoreductase, a flavin nucleoside coenzyme, and a mediator formulation. The mediator formulation comprises at least one electroactive organic molecule independently selected from a phenoxazine or a phenoxazinium salt and at least one coordination complex.

In a twelfth principal aspect, the present invention provides a method of making a test strip for testing a blood sample. The method comprises depositing a first electrode on a base; depositing a second electrode on the base; and applying a reagent layer on the base covering at least a portion of at least first or second electrode. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a benzophenoxazine or a benzophenoxazinium salt and at least one coordination complex independently selected from iron, osmium or ruthenium complexes.

In a thirteenth principal aspect, the present invention provides a method of making a test strip for testing a blood sample. The method comprises depositing a first electrode on a base; depositing a second electrode on the base; and applying a reagent layer on the base covering at least a portion of at least first or second electrode. The reagent layer comprises a glucose oxidoreductase, a flavin nucleoside coenzyme and/or a nicotinamide nucleotide coenzyme, and a mediator formulation. The mediator formulation comprises at least one electroactive organic molecule independently selected from a benzophenoxazine or a benzophenoxazinium salt and at least one ruthenium coordination complex.

In a fourteenth principal aspect, the present invention provides a method of making a test strip for testing a blood sample. The method comprises depositing a first electrode on a base; depositing a second electrode on the base; and applying a reagent layer on the base covering at least a portion of at least first or second electrode. The reagent layer comprises a glucose oxidoreductase, a flavin nucleoside coenzyme and/or a nicotinamide nucleotide coenzyme, and a mediator formulation. The mediator formulation comprises at least one electroactive organic molecule and at least one coordination complex. The at least one electroactive organic molecule is independently selected from 9-(dimethylamino)benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine. The at least one coordination complex is ruthenium hexamine.

In a fifteenth principal aspect, the present invention provides a method of making a test strip for testing a blood sample. The method comprises depositing a first electrode on a base; depositing a second electrode on the base; and applying a reagent layer on the base covering at least a portion of at least first or second electrode. The reagent layer comprises glucose dehydrogenase, flavin adenine dinucleotide and/or nicotinamide adenine dinucleotide, and a mediator formulation. The mediator formulation comprises at least one electroactive organic molecule independently selected from a benzophenoxazine or a benzophenoxazinium salt and at least one ruthenium coordination complex.

In a sixteenth principal aspect, the present invention provides for a meter for use in combination with a test strip for measuring a glucose level in a blood sample applied to a sample chamber in a test strip, said test strip comprising a base, a working electrode, a counter electrode, and at least one reagent layer, wherein the at least one reagent layer comprises glucose dehydrogenase, flavin adenine dinucleotide and/or nicotinamide adenine dinucleotide, and a mediator formulation, said mediator formulation comprising at least one electroactive organic molecule and at least one coordination complex, wherein the at least one electroactive organic molecule is independently selected from a benzophenoxazine or a benzophenoxazinium salt, and the at least one at least one coordination complex is a ruthenium complex. The meter comprises a first connector for receiving said test strip, a second connector for receiving a removable data storage device, a processor, a display and at least one electrode for applying at least a first voltage between said working and counter electrodes when said test strip is inserted.

In a seventeenth principal aspect, the present invention provides for a meter for use in combination with a test strip for measuring a glucose level in a blood sample applied to a sample chamber in a test strip, said test strip comprising a base, a working electrode, a counter electrode, and at least one reagent layer, wherein the at least one reagent layer comprises a glucose oxidoreductase, a flavin nucleoside coenzyme and/or a nicotinamide nucleotide coenzyme, and a mediator formulation, said mediator formulation comprising at least one electroactive organic molecule and at least one coordination complex, wherein the at least one electroactive organic molecule is independently selected from 9-(dimethylamino)benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine, and the at least one coordination complex is ruthenium hexamine. The meter comprises a first connector for receiving said test strip, a second connector for receiving a removable data storage device, a processor, a display and at least one electrode for applying at least a first voltage between said working and counter electrodes when said test strip is inserted.

It is to be understood that both the foregoing general description and the following detailed description are exemplary and explanatory only and are not restrictive of the invention, as claimed.

The accompanying drawing which is incorporated in and constitutes a part of this specification, illustrate one (several) embodiment(s) of the invention and together with the description, serve to explain the principles of the invention.

DESCRIPTION OF THE EMBODIMENTS

Figure 1:
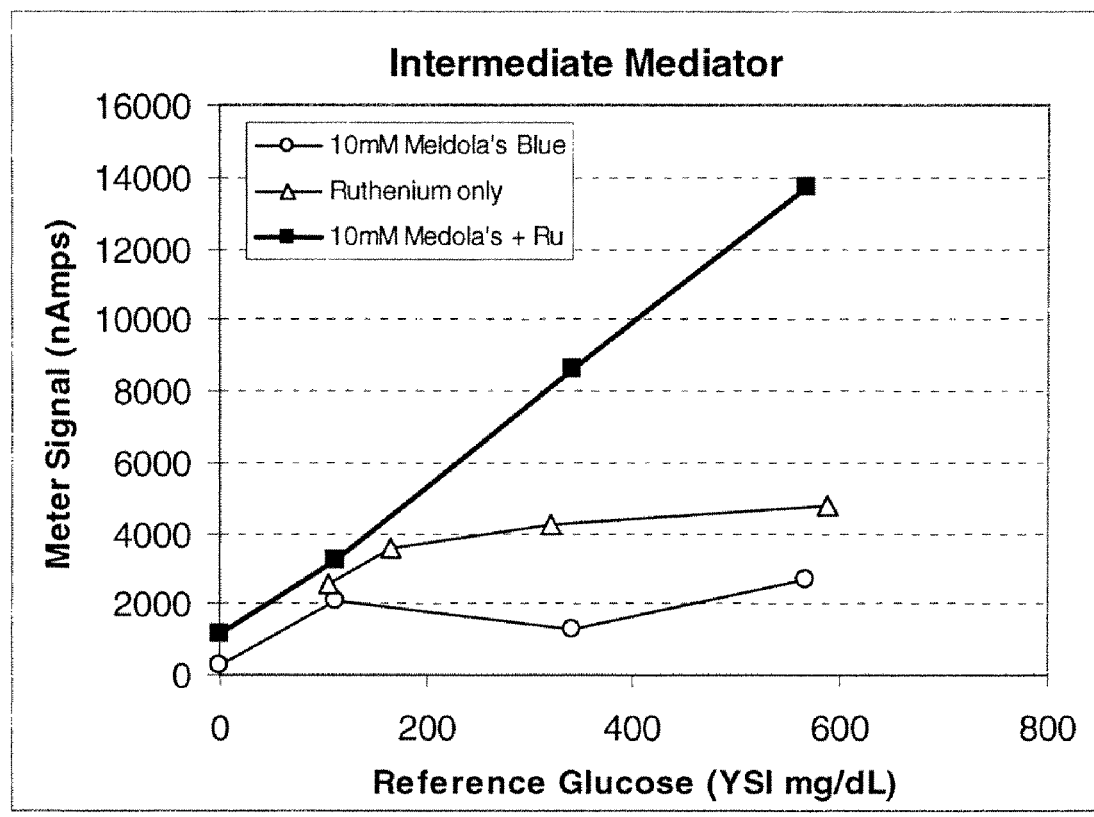
FIG. 1 is a graph of measured current as a function of glucose concentration for sensor strips having different mediator formulations.

Reference will now be made in detail to the exemplary embodiments of the invention, examples of which are illus-trated in the accompanying drawings. Wherever possible, the same reference numbers will be used throughout the drawings to refer to the same or like parts.

In accordance with exemplary embodiments, a reagent composition is provided for use in an electrochemical sensor for measuring the glucose level in a sample. The sensor further includes a test strip and a meter. The test strip includes a working electrode and a counter electrode, with at least one of the electrodes being partially covered by the reagent composition to form a reagent layer. The reagent layer includes an oxidoreductase, a coenzyme, and a mediator formulation. The mediator formulation comprises at least one electroactive organic molecule and at least one coordination complex. Reagent layers of the present invention may provide for improvements in accuracy, sensitivity, range of analysis, and stability.

A "sample" may include a composition containing an unknown amount of the analyte (e.g., glucose) of interest. Typically, a sample for electrochemical analysis is in liquid form, and preferably the sample is an aqueous mixture. A sample may be a biological sample, such as blood, urine or saliva. A sample may be a derivative of a biological sample, such as an extract, a dilution, a filtrate, or a reconstituted precipitate.

A "mediator" may include a substance that can be oxidized or reduced and that can transfer one or more electrons between a first substance and a second substance. A mediator is a reagent in an electrochemical analysis and is not the analyte of interest. In a simple system, the mediator undergoes a redox reaction with the oxidoreductase after the oxidoreductase has been reduced or oxidized through its contact with an appropriate substrate. This oxidized or reduced mediator then undergoes the opposite reaction at the electrode and is regenerated to its original oxidation number.

An "oxidoreductase" may include any enzyme that facilitates the oxidation or reduction of a substrate. Oxidoreductases may include "oxidases," which facilitate oxidation reactions in which molecular oxygen is the electron acceptor; "reductases," which facilitate reduction reactions in which the analyte is reduced and molecular oxygen is not the analyte; and "dehydrogenases," which facilitate oxidation reactions in which molecular oxygen is not the electron acceptor. See, for example, *Oxford Dictionary of Biochemistry and Molecular Biology*, Revised Edition, A. D. Smith, Ed., New York: Oxford University Press (1997) pp. 161, 476, 477, and 560, which is herein incorporated by reference in its entirety. Examples of oxidoreductases includes glucose dehydrogenase (GDH), glucose oxidase, cholesterol esterase, lipoprotein lipase, glyceral kinase, lactate oxidase, pyruvate oxidase, alcohol oxidase, uricase, and the like. In one embodiment of the present invention the oxidoreductase is selected from GDH and glucose oxidase.

A "coordination complex" may include a complex having well-defined coordination geometry, such as octahedral or square planar geometry. Unlike organotransition metal complexes, which are defined as complexes where a transition metal is bonded to at least one carbon atom through a sigma bond, coordination complexes are defined by their geometry. Thus, coordination complexes may be organotransition metal complexes (such as ferricyanide (III) and its reduced ferrocyanide (II) counterpart), or complexes where non-metal atoms other than carbon, such as heteroatoms including nitrogen, sulfur, oxygen, and phosphorous, are datively bonded to the transition metal center. For example, ruthenium hexaamine is a coordination complex having a well-defined octahedral geometry where six $NH_3$ ligands (formal charge of 0 on each of the 6 ligands) are datively bonded to the ruthenium center. A more complete discussion of organotransition metal complexes, coordination complexes, and transition metal bonding may be found in Collman et al., *Principles and Applications of Organotransition Metal Chemistry* (1987) and Miessler & Tarr, *Inorganic Chemistry* (1991), which are herein incorporated by reference in their entireties. In one embodiment of the present invention the coordination complex is selected from iron, ruthenium and osmium complexes.

A "coenzyme" may include a non-protein redox prosthetic. Coenzymes of the present invention are preferably organic molecules that are linked covalently or noncovalently to an enzyme and are changed, for example, oxidized or reduced, by the conversion of the analyte. Examples of coenzymes are flavin, nicotinamide and quinone derivatives, for example: flavin nucleoside derivatives such as FAD, $FADH_2$, FMN, $FMNH_2$, etc.; nicotinamide nucleotide derivatives such as NAD, $NADH/H^+$, NADP, $NADPH/H_2$; or ubiquinones such as coenzyme Q or PQQ. In one embodiment of the present invention the coenzyme is a flavin nucleoside. In another embodiment, the coenzyme is a nicotinamide nucleotide.

An "electroactive organic molecule" may include an organic molecule that does not contain a metal and that is capable of undergoing an oxidation or reduction reaction. Electroactive organic molecules can behave as redox species and as mediators. Examples of electroactive organic molecules include benzoquinones and naphthoquinones, N-oxides, nitroso compounds, hydroxylamines, oxines, phenazines, phenothiazines, phenoxazines, indophenols, and indamines. Other examples of electroactive organic molecules include those described in U.S. Pat. No. 5,520,786, which is herein incorporated by reference in its entirety. In one embodiment of the present invention at least one electroactive organic molecule is independently selected from phenazines, phenothiazines, or phenoxazines, or salts thereof (e.g., phenoxazinium salts). Phenoxazines and their salts include, but are not limited to, benzophenoxazines and their corresponding salts (i.e., benzophenoxazinium salts). In a preferred embodiment, the at least one electroactive organic molecule is a benzophenoxazinium salt. Exemplary benzophenoxazines and benzophenoxzinium salts include, but are not limited to, 9-(dimethylamino)benzophenoxazin-7-ium chloride, N-(9H-benzophenoxazin-9-ylidene)-N-methylmethanaminium chloride, 8-dimethylamino-2,3-benzophenoxazine, 8-dimelthylamino-1,2-benzophenoxazine, 8-dimelthylamino-1,2-benzophenoxazine hemi (zinc chloride) salt, 1,2-benzophenoxazine, 7-dimethylamino-1,2-benzophenoxazine and/or 9-diethylamino-5-amino-benzophenoxazine (Nile Blue).

In a preferred embodiment, glucose dehydrogenase (GDH) and flavin adenine dinucleotide (FAD) comprise the oxidoreductase-coenzyme combination. In another preferred embodiment, GDH and nicotinamide adenine dinucleotide ($NAD^+$) comprise the oxidoreductase-coenzyme combination. In addition, a mediator formulation comprising an electroactive organic molecule and a coordination complex may be incorporated into the reagent layer with the oxidoreductase-coenzyme. In a preferred embodiment, a benzophenoxazinium salt (e.g., Meldola's Blue) and a ruthenium complex (e.g., ruthenium hexaamine) are combined with GDH-FAD. In another preferred embodiment, a benzophenoxazinium salt (e.g., Meldola's Blue) and a ruthenium complex (e.g., ruthenium hexaamine) are combined with $GDH-NAD^+$.

Optionally, the reagent composition may include inert ingredients that are not directly involved in any oxidation-reduction reactions in the electrochemical sensor. Examples of such inert ingredients include binding agents, thickening agents, and buffering components. Binding agents may include bentone, polyethylene oxide, and/or carbomethyl cellulose. Thickening agents may include silica and/or polyethylene oxide. Buffering components may be made up of one or more, e.g., two, three, four or more, distinct buffering agents, where the buffering component stabilizes the mediator during storage of the composition in dry form such that little if any of the mediator is reduced prior to use, e.g., during storage. A buffer is considered to stabilize a mediator if, in the presence of the buffer, little if any of the mediator converts to a reduced form over a given storage period. Suitable buffers are buffers that do not cause the background signal in an electrochemical test to increase over time. The background signal is the signal obtained when analyte-free sample is introduced to the electrochemical testing system.

In addition, the reagent composition may further include a wetting agent. In one embodiment, the wetting agent is used in combination with a detergent. Wetting agents may be added to facilitate uniform coating of the reagent composition onto an electrochemical test strip. A plurality of one or more of the combination of agents may also be used. The agents used may improve dissolution of the assay reagents as well as enhance the wicking properties of a capillary fill strip. The agents include those known in the art, for example, polymers, anti-foaming agents, and surfactants. Representative types of surfactants/detergents of interest include, but are not limited to: Tritons, Macols, Tetronics, Silwets, Zonyls, and Pluronics. Suitable agents include Pluronic materials which are block co-polymers of polyethylene oxide and polypropylene oxide. Examples of Pluronic materials include Pluronic P103 which has good wetting properties and Pluronic F87 Prill which has good detergent properties. Both Pluronic P103 and F87 Prill also have a cloud point temperature greater than 80° C. which is desirable since this property avoids a phase change in the composition during the drying process.

Some reagent compositions may also include one or more enzyme cofactors. Enzyme cofactors of interest include divalent metal cations such as $Ca^{2+}$ and/or $Mg^{2+}$.

Stabilizers may also be added to the reagent composition to help stabilize the enzyme and prevent denaturation of the protein. The stabilizer may also help stabilize the redox state of the mediator, in particular, the oxidized redox mediator. Examples of stabilizing agents include, but are not limited to carbohydrates (e.g. sucrose, trehalose, mannitol, and lactose), amino acids, proteins (e.g. BSA and albumin) and organic compounds such as EDTA and the like.

Viscosity modifiers may also be added to the reagent to modify the liquid reagent rheology. Examples of such agents include poly(acrylic acid), poly(vinyl alcohol), dextran, and/or BSA.

In another embodiment, the invention relates to an electrochemical sensor for measuring an analyte. The sensor includes a test strip and a meter. The test strip includes a reagent layer comprising at least one of the reagent compositions described herein. An individual test strip may also include an embedded code relating to data associated with a lot of test strips, or data particular to that individual strip. Such coded strips are further described in U.S. Pat. Pub. No. 2007/0015286, which is herein incorporated by reference in its entirety.

The test strip may include a sample chamber for receiving a user's fluid sample, such as, for example, a blood sample. The sample chamber and test strip can be formed using materials and methods described in commonly owned U.S. Pat. No. 6,743,635, which is herein incorporated by reference in its entirety. Accordingly, the sample chamber may include a first opening in the proximal end of the test strip and a second opening for venting the sample chamber. The sample chamber may be dimensioned so as to be able to draw the blood sample in through the first opening, and to hold the blood sample in the sample chamber, by capillary action. The test strip can include a tapered section that is narrowest at the proximal end, or can include other indicia in order to make it easier for the user to locate the first opening and apply the blood sample.

The meter may be battery powered and may stay in a low-power sleep mode when not in use in order to save power. When the test strip is inserted into the meter, the first and second plurality of electrical contacts on the test strip contact corresponding electrical contacts in the meter. The second plurality of electrical contacts may bridge a pair of electrical contacts in the meter, causing a current to flow through the a portion of the second plurality of electrical contacts. The current flow through the second plurality of electrical contacts causes the meter to wake up and enter an active mode. The meter also reads the code information provided by the second plurality and can then identify, for example, the particular test to be performed, or a confirmation of proper operating status. In addition, the meter can also identify the inserted strip as either a test strip or a check strip based on the particular code information. If the meter detects a check strip, it performs a check strip sequence. If the meter detects a test strip, it performs a test strip sequence.

In the test strip sequence, the meter validates the working electrode, counter electrode, and, if included, the fill-detect electrodes, by confirming that there are no low-impedance paths between any of these electrodes. If the electrodes are valid, the meter indicates to the user that the sample may be applied to the test strip. The meter then applies a drop-detect voltage between the working and counter electrodes and detects a fluid sample, for example, a blood sample, by detecting a current flow between the working and counter electrodes (i.e., a current flow through the blood sample as it bridges the working and counter electrodes). To detect that an adequate sample is present in the sample chamber and that the blood sample has traversed the reagent layer and mixed with the chemical and biological constituents in the reagent layer, the meter may apply a fill-detect voltage between the fill-detect electrodes and measures any resulting current flowing between the fill-detect electrodes. If this resulting current reaches a sufficient level within a predetermined period of time, the meter indicates to the user that adequate sample is present and has mixed with the reagent layer.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the formulation in the reagent layer, and the resulting current is related to the concentration of the particular constituent measured, such as, for example, the glucose level in a blood sample.

In one example, the reagent layer may react with glucose in the blood sample in order to determine the particular glucose concentration. In one example, glucose dehydrogenase (GDH) and flavin adenine dinucleotide (FAD) are used in the reagent layer. The recitation of GDH-FAD is intended as an example only and other materials can be used without departing from the scope of the invention. Other possible mediator combinations may be used in addition to the oxidoreductase-coenzyme combination. For example, a phenoxazine (e.g., a benzophenoxazine) and a coordination complex (e.g. a ruthenium complex) may be incorporated into the reagent layer with GDH-FAD. During a sample test, the GDH initiates a reaction that oxidizes the glucose to gluconic acid and reduces the coordination complex (e.g., ruthenium (III) to ruthenium (II)). When an appropriate voltage is applied to a working electrode, relative to a counter electrode, the reduced coordination complex (e.g., ruthenium (II)) is oxidized (e.g., ruthenium (III)), thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user.

Exemplary Embodiments of the Invention

In one embodiment, the reagent layer may react with glucose in the blood sample in order to determine the particular glucose concentration. The reagent layer comprises an oxidoreductase, a coenzyme, and a mediator formulation. The mediator formulation comprises at least one electroactive organic molecule and at least one coordination complex. The at least one electroactive organic molecule may be independently selected from phenazines, phenothiazines, phenoxazines, or salts thereof. The at least one coordination complex may be independently selected from iron, osmium or ruthenium complexes. In a preferred embodiment, the at least one electroactive organic molecule is a phenoxazinium salt and the at least one coordination complex is a ruthenium complex.

In another embodiment, the reagent layer comprises an oxidoreductase, a coenzyme, and a mediator formulation, wherein oxidoreductase is glucose oxidoreductase and the coenzyme is selected from a flavin nucleoside and/or a nicotinamide nucleotide. The mediator formulation comprises at least one electroactive organic molecule and at least one coordination complex. The at least one electroactive organic molecule may be independently selected from phenazines, phenothiazines, phenoxazines, or salts thereof, while the at least one coordination complex is independently selected from iron, osmium or ruthenium complexes. In a preferred embodiment, the at least one electroactive organic molecule is a phenoxazinium salt and the at least one coordination complex is a ruthenium complex.

In another embodiment, the reagent layer comprises an oxidoreductase, a coenzyme, and a mediator formulation, wherein the oxidoreductase is glucose dehydrogenase (GDH) and the coenzyme is selected from flavin adenine dinucleotide ($FAD^+$) and/or nicotinamide adenine dinucleotide ($NAD^+$). The mediator formulation comprises at least one electroactive organic molecule and at least one coordination complex. The at least one electroactive organic molecule may be a phenoxazinium salt and the at least one coordination complex may be a ruthenium complex. In a preferred embodiment, the ruthenium complex is ruthenium hexamine.

In another embodiment, the reagent layer comprises an oxidoreductase, a coenzyme, and a mediator formulation, wherein the oxidoreductase is glucose dehydrogenase (GDH) and the coenzyme is selected from flavin adenine dinucleotide ($FAD^+$) and/or nicotinamide adenine dinucleotide ($NAD^+$). The mediator formulation comprises at least one electroactive organic molecule and at least one coordination complex. The at least one electroactive organic molecule may be a phenoxazine or a salt thereof, and the at least one coordination complex may be a ruthenium complex. In a preferred embodiment, the at least one electroactive organic molecule is a benzophenoxazine or a salt thereof.

In another embodiment, the reagent layer comprises an oxidoreductase, a coenzyme, and a mediator formulation, wherein the oxidoreductase is glucose dehydrogenase (GDH) and the coenzyme is selected from flavin adenine dinucleotide ($FAD^+$) and/or nicotinamide adenine dinucleotide ($NAD^+$). The mediator formulation comprises at least one electroactive organic molecule and at least one coordination complex. The at least one electroactive organic molecule may be a benzophenoxazine or a salt thereof, and the at least one coordination complex may be a ruthenium complex. In a preferred embodiment, the at least one electroactive organic molecule is independently selected from 9-(dimethylamino) benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine.

In another embodiment, the reagent layer comprises an oxidoreductase, a coenzyme, and a mediator formulation, wherein the oxidoreductase is glucose dehydrogenase (GDH) and the coenzyme is selected from flavin adenine dinucleotide ($FAD^+$) and/or nicotinamide adenine dinucleotide ($NAD^+$). The mediator formulation comprises at least one electroactive organic molecule and at least one coordination complex. The at least one electroactive organic molecule may be independently selected from 9-(dimethylamino)benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine, and the at least one coordination complex may be a ruthenium complex. In a preferred embodiment, the at least one coordination complex is ruthenium hexamine.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A reagent for detecting an analyte, comprising:
   a glucose oxidoreductase;
   a coenzyme selected from a flavin nucleoside and a nicotinamide nucleotide; and
   a mediator formulation comprising at least one electroactive organic molecule independently selected from a phenoxazine or a phenoxazinium salt, and at least one coordination complex selected from osmium and ruthenium complexes.

2. The reagent according to claim 1, wherein the coenzyme is flavin adenine dinucleotide.

3. The reagent according to claim 1, wherein the glucose oxidoreductase is glucose dehydrogenase.

4. The reagent according to claim 1, wherein the at least one electroactive organic molecule is independently selected from a benzophenoxazine or a benzophenoxazinium salt.

5. The reagent according to claim 1, wherein the at least one coordination complex is a ruthenium complex.

6. The reagent according to claim 1, wherein the coenzyme is nicotinamide adenine dinucleotide.

7. A reagent for detecting an analyte, comprising:
   a glucose oxidoreductase;
   a coenzyme selected from a flavin nucleoside and a nicotinamide nucleotide; and
   a mediator formulation comprising at least one electroactive organic molecule independently selected from a benzophenoxazine or a benzophenoxazinium salt, and at least one coordination complex independently selected from osmium and ruthenium complexes.

8. The reagent according to claim 7, wherein the glucose oxidoreductase is a glucose dehydrogenase.

9. The reagent according to claim 7, wherein the coenzyme is flavin adenine dinucleotide.

10. The reagent according to claim 7, wherein the coordination complex is a ruthenium complex.

11. The reagent according to claim 7, wherein the at least one electroactive organic molecule is independently selected from 9-(dimethylamino)benzophenoxazin-7-ium chloride, N-(9H-benzophenoxazin-9-ylidene)-N-methylmethanaminium chloride, or 8-dimethylamino-2,3-benzophenoxazine.

12. The reagent according to claim 7, wherein the coenzyme is nicotinamide adenine dinucleotide.

13. A reagent for detecting an analyte, comprising:
    a glucose oxidoreductase;
    a coenzyme selected from a flavin nucleoside and a nicotinamide nucleotide; and
    a mediator formulation comprising at least one electroactive organic molecule independently selected from a benzophenoxazine or a benzophenoxazinium salt, and at least one ruthenium coordination complex.

14. The reagent according to claim 13, wherein the glucose oxidoreductase is a glucose dehydrogenase.

15. The reagent according to claim 13, wherein the flavin nucleoside coenzyme is flavin adenine dinucleotide.

16. The reagent according to claim 13, wherein the coordination complex is ruthenium hexamine.

17. The reagent according to claim 13, wherein the at least one electroactive organic molecule is independently selected from 9-(dimethylamino)benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine.

18. The reagent according to claim 13, wherein the coenzyme is nicotinamide adenine dinucleotide.

19. A reagent for detecting an analyte, comprising:
    glucose dehydrogenase;
    a coenzyme selected from flavin adenine dinucleotide and nicotinamide adenine dinucleotide; and
    a mediator formulation comprising at least one electroactive organic molecule independently selected from a benzophenoxazine or a benzophenoxazinium salt, and at least one ruthenium complex.

20. The reagent according to claim 19, wherein the at least one electroactive organic molecule is independently selected from 9-(dimethylamino)benzophenoxazin-7-ium chloride, N-(9H-benzophenoxazin-9-ylidene)-N-methylmethanaminium chloride, 8-dimelthylamino-2,3-benzophenoxazine hemi (zinc chloride) salt, 7-dimethylamino-1,2-benzophenoxazine or 8-dimethylamino-2,3-benzophenoxazine.

21. The reagent according to claim 19, wherein the at least one ruthenium complex is ruthenium hexamine.

22. The reagent according to claim 20, wherein the at least one ruthenium complex is ruthenium hexamine.

* * * * *